(12) United States Patent
Ismailoglu et al.

(10) Patent No.: US 9,272,072 B1
(45) Date of Patent: Mar. 1, 2016

(54) OSTEOINDUCTIVE BONE GRAFT SUBSTITUTE

(71) Applicant: NuVasive, Inc., San Diego, CA (US)

(72) Inventors: Ali Ismailoglu, San Diego, CA (US); Frank Vizesi, San Diego, CA (US); Sung-Ching Chen, New Taipei (TW); Po-Hung Lai, New Taipei (TW); Kehsin Chien, New Taipei (TW)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/697,443

(22) Filed: Apr. 27, 2015

Related U.S. Application Data

(63) Continuation of application No. 14/059,437, filed on Oct. 21, 2013, now abandoned.

(60) Provisional application No. 61/716,428, filed on Oct. 19, 2012.

(51) Int. Cl.
*A61L 27/46* (2006.01)
*A61L 27/54* (2006.01)

(52) U.S. Cl.
CPC .............. *A61L 27/46* (2013.01); *A61L 27/54* (2013.01); *A61L 2300/112* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,497,075 A | 2/1985 | Niwa | |
| 4,693,986 A | 9/1987 | Vit | |
| 4,990,333 A | 2/1991 | Lane | |
| 5,001,169 A | 3/1991 | Nathan | |
| 5,064,436 A | 11/1991 | Ogiso | |
| 5,204,382 A | 4/1993 | Wallace | |
| 5,352,715 A | 10/1994 | Wallace | |
| 5,374,539 A | 12/1994 | Minmi | |
| 5,425,770 A | 6/1995 | Piez | |
| 6,201,039 B1 | 3/2001 | Brown | |
| 6,506,217 B1 | 1/2003 | Arnett | |

(Continued)

FOREIGN PATENT DOCUMENTS

| | | |
|---|---|---|
| EP | 0267624 A2 | 5/1988 |
| JP | 04212369 A | 8/1992 |

(Continued)

OTHER PUBLICATIONS

Foltran et al., "Novel Biologically Inspired Collagen Nanofibers Reconstituted by Electrospinning Method," Macromol. Symp. (2008) vol. 269, pp. 111-118.

(Continued)

*Primary Examiner* — Carlos Azpuru
*Assistant Examiner* — Casey Hagopian
(74) *Attorney, Agent, or Firm* — Jonathan Spangler; Jennifer Russell

(57) ABSTRACT

An osteoinductive bone graft substitute including an osteoinductive calcium phosphate component retained within a collagen scaffold, wherein the collagen scaffold is formulated to maintain the osteoinductivity of the calcium phosphate component while also exhibiting the following characteristics (1) ability to absorb bone marrow and/or other physiologic liquids, (2) compression resistance; (3) moldability; (4) retaining the calcium phosphate component during and after manipulation of the collagen scaffold and (5) fibrous collagen matrix that retains but does not occlude the osteoinductive calcium phosphate component.

5 Claims, 3 Drawing Sheets

(56) References Cited

U.S. PATENT DOCUMENTS

| | | |
|---|---|---|
| 6,511,510 B1 | 1/2003 | de Bruijn et al. |
| 6,599,516 B1 | 7/2003 | Knaack |
| 6,652,887 B1 | 11/2003 | Richelsoph |
| 6,679,918 B1 | 1/2004 | Benedict |
| 7,105,182 B2 | 9/2006 | Szymaitis |
| 7,156,880 B2 | 1/2007 | Evans |
| 7,166,133 B2 | 1/2007 | Evans |
| 7,189,263 B2 | 3/2007 | Erbe |
| 7,229,971 B2 | 6/2007 | Tanaka |
| 7,235,107 B2 | 6/2007 | Evans |
| 7,241,316 B2 | 7/2007 | Evans |
| 7,381,224 B1 | 6/2008 | Li |
| 7,534,451 B2 | 5/2009 | Erbe |
| 7,544,212 B2 | 6/2009 | Li |
| 7,547,449 B2 | 6/2009 | Gower |
| 7,942,934 B2 | 5/2011 | Yuan |
| 2003/0199615 A1 | 10/2003 | Chaput |
| 2005/0031704 A1 | 2/2005 | Ahn |
| 2005/0142163 A1 | 6/2005 | Hunter |
| 2005/0191226 A1 | 9/2005 | Tuan |
| 2006/0292200 A1 | 12/2006 | Delaney |
| 2007/0009557 A1 | 1/2007 | Kuhn |
| 2009/0265017 A1* | 10/2009 | McKay .............. A61F 2/2803 623/23.63 |

FOREIGN PATENT DOCUMENTS

| | | |
|---|---|---|
| WO | WO-99/34844 A1 | 7/1999 |
| WO | WO-2006/115398 A1 | 11/2006 |
| WO | WO-2007/094672 A1 | 8/2007 |

OTHER PUBLICATIONS

Gelman et al., "Collagen fibril formation in Vitro. The role of the nonhelical terminal regions," (1979) J Biol Chem 254(22): 11741-11745.

Habibovic et al., Biomaterials (2005) 26(17):3565-3575.

Miao et al., "Porous calcium phosphate ceramics prepared by coating polyurethane foams with calcium phosphate cements," Materials Lett. (2004) vol. 58, pp. 397-402.

Piez, Ka "Collagen," Reprinted from Encyclopedia of Polymer Science and Engineering (1985) vol. 3, Second Edition, pp. 699-727.

Tai et al., "Prospective analysis of secondary alveolar bone grafting using computed tomography," J Oral Maxillofac Surg., (2000) vol. 58, No. 11, pp. 124-129. (abstract only).

Tang et al., "Applied anatomy of the V-shaped fibular osteomyocutaneous flap in reconstruction of the hindfoot," Radial. Anat. (2001) vol. 23, No. 4, pp. 215-220.

Yamasaki et al., "Osteogenic response to porous hydroxyapatite ceramics under the skin of dogs," Biomaterials (1992) 13:308-312.

* cited by examiner

OSTEOINDUCTIVE BONE GRAFT SUBSTITUTE

CROSS REFERENCE TO RELATED APPLICATIONS

This application is a continuation of U.S. patent application Ser. No. 14/059,437, filed on Oct. 21, 2013, which claims the benefit of the filing date of U.S. Provisional Patent Application No. 61/716,428 which was filed on Oct. 19, 2012. The content of U.S. application Nos. 14/059,437 and 61/716,428 is incorporated by reference as part of this application.

FIELD

This application relates generally to bone graft substitutes and more specifically toward an osteoinductive bone graft substitute comprising a calcium phosphate component and a collagen matrix.

SUMMARY

The present application is directed toward an osteoinductive bone graft substitute comprising a calcium phosphate component and a collagen matrix. The osteoinductive bone graft substitute includes an osteoinductive calcium phosphate component retained within a collagen scaffold, wherein the collagen scaffold is formulated to maintain the osteoinductivity of the calcium phosphate component while also exhibiting the following characteristics (1) ability to absorb bone marrow and/or other physiologic liquids, (2) compression resistance; (3) moldability; (4) retaining the calcium phosphate component during and after manipulation of the collagen scaffold and (5) fibrous collagen matrix that retains but does not occlude the osteoinductive calcium phosphate component. The osteoinductive bone graft substitute described herein is greater than 70% porous and is inherently osteoinductive (i.e. it does not require the addition of bone marrow aspirate to be osteoinductive).

DETAILED DESCRIPTION

Figure 2:
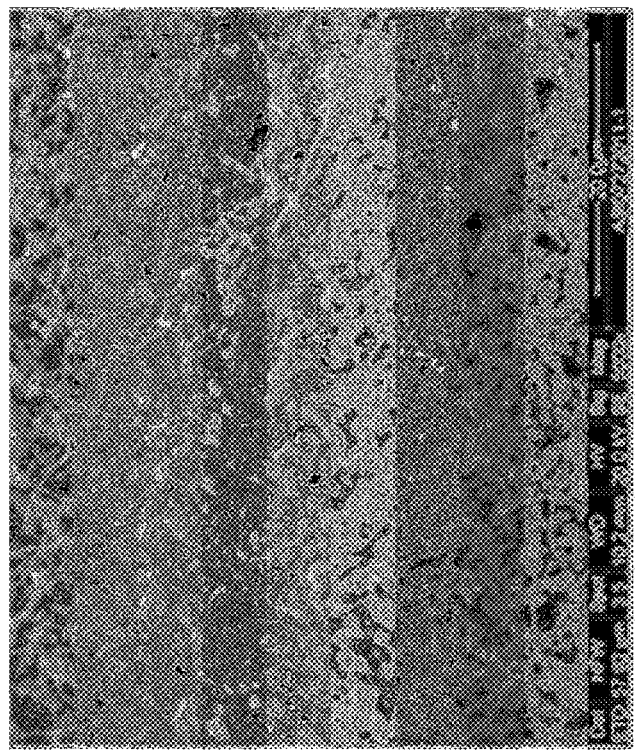
FIG. 2 is a scanning electron micrograph of a bone graft substitute comprising the calcium phosphate granules of FIG. 1 and a collagen matrix.
Figure 1:
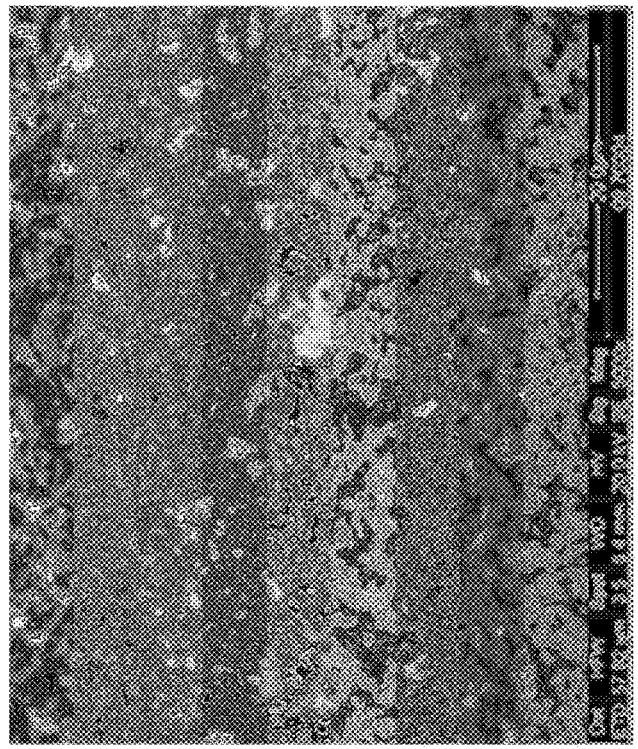
FIG. 1 is a scanning electron micrograph of calcium phosphate granules according to a first embodiment of the bone graft substitute.
Figure 4:
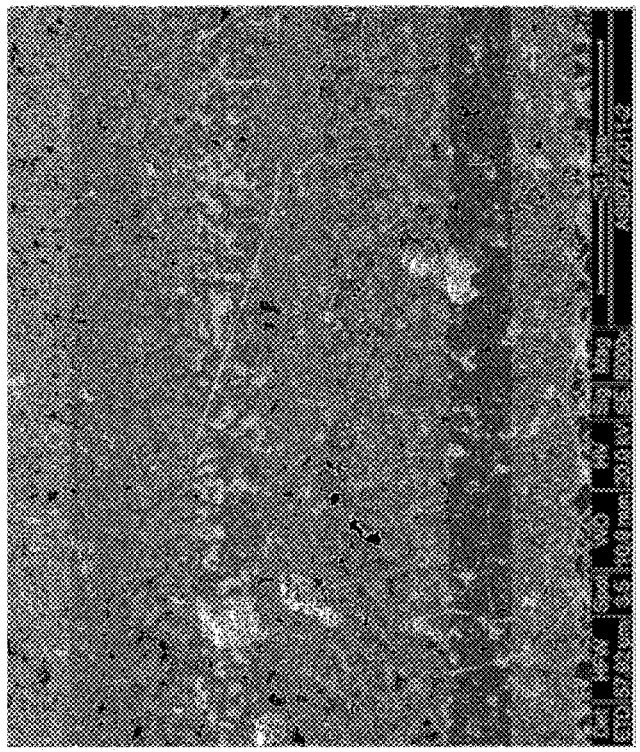
FIG. 4 is a scanning electron micrograph of a bone graft substitute comprising the calcium phosphate granules of FIG. 3 and a collagen matrix.
Figure 3:
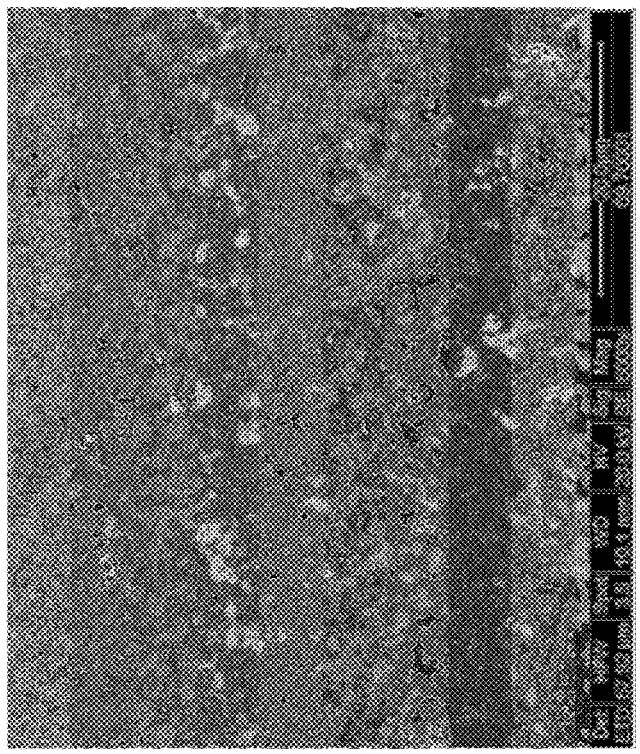
FIG. 3 is a scanning electron micrograph of calcium phosphate granules according to an alternative embodiment of the bone graft substitute.
Figure 6:
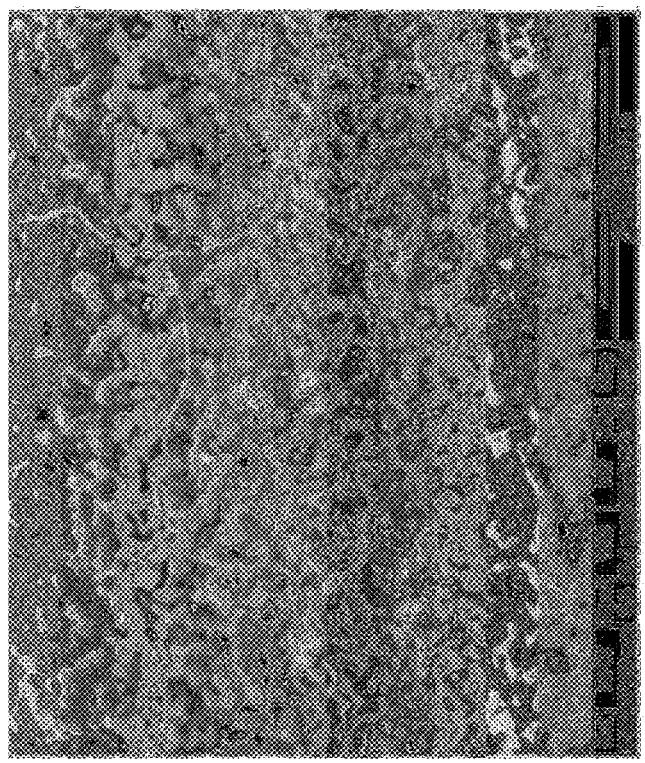
FIG. 6 is a scanning electron micrograph of a bone graft substitute comprising the calcium phosphate granules of FIG. 5 and a collagen matrix.
Figure 5:
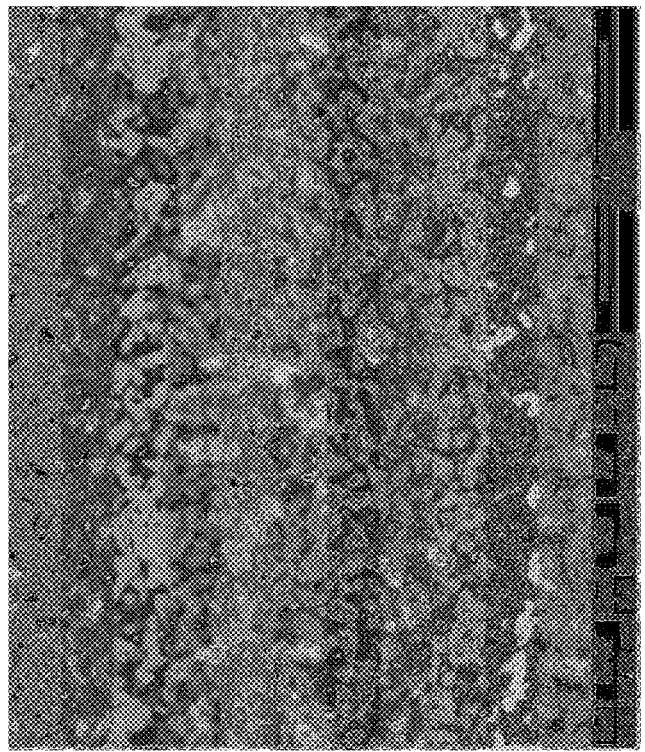
FIG. 5 is a scanning electron micrograph of calcium phosphate granules according to another alternative embodiment of the bone graft substitute.

According to an exemplary embodiment, the calcium phosphate component of the osteoinductive bone graft substitute is an osteoinductive calcium phosphate, such as the calcium phosphate described in U.S. Pat. No. 7,942,934, which is hereby incorporated by reference in its entirety. However, other osteoinductive calcium phosphates may be also be used with the collagen matrix formulation described in the examples herein to achieve an osteoinductive bone graft substitute.

EXAMPLE 1

Handling Characteristics of Scaffold Prototypes

Preparation of the Materials

Five bone graft substitute prototypes were manufactured according to different formulations using variable collagen compositions, collagen and granules concentrations and crosslinking times, as shown in Table 1. The granule particle size range was between 500 μm and 1000 μm. Lyophilization was followed by dihydrothermal (DHT) crosslinking treatment in all samples. Lyophilization was performed, according to Table 2. DHT temperature was 110° C. for all formulations. All prototypes were gamma sterilized (25-30 kGy). After sterilization, each prototype was hydrated in preparation of handling evaluation. Hydration of prototypes was performed by placing each prototype in a petri dish and soaking with 5 cc of heparinized sheep blood.

TABLE 1

| | Formulation Table | | | | | | |
|---|---|---|---|---|---|---|---|
| Prototype ID | Collagen Composition | Conc (mg/ml) | Collagen Final wt % | Granule Final wt % | Collagen Slurry (ml) | Granule (gr) | DHT (days) |
| Formulation 1 | Acid 50%/ Pepsin 50% | 65 | 16 | 84 | 75 | 25 | 1 |
| Formulation 2 | Acid 80%/ Pepsin 20% | 65 | 16 | 84 | 75 | 25 | 1 |
| Formulation 3 | Acid Swollen | 30 | 20 | 80 | 89 | 11 | 0 |
| Formulation 4 | Acid Swollen | 50 | 12 | 88 | 73 | 27 | 0 |
| Formulation 5 | Pepsin Treated | 65 | 16 | 84 | 75 | 25 | 3 |

TABLE 2

| | Lyophilization Program | | |
|---|---|---|---|
| | Temp (° C.) | Vacuum (mT) | Time (min) |
| Initial | −50 | 100 | 30 |
| Phase I | −35 | 200 | 120 |
| | −25 | 200 | 360 |
| | −18 | 200 | 480 |
| | −10 | 200 | 480 |
| | −6 | 200 | 480 |
| | 0 | 200 | 720 |
| Phase II | 25 | 200 | 600 |

Physical Handling of the Samples

In order to determine the optimal prototype formulation, each prototype was evaluated based on its response to physical handling. Prototype samples were bended, twisted, pulled and gently compressed to simulate handling conditions. Handling properties which were evaluated included compression resistance when wet, cohesiveness, moldability, flexibility and strength.

Handling properties of the prototypes were evaluated on a score from one (1) to five (5), with 1 being "poor" and 5 being "excellent." Each prototype was evaluated three (3) times, each time by a different expert user.

Results of Physical Handling

Results of the physical handling of each prototype are shown in Tables 3 and 4.

TABLE 3

| | Handling Properties - Average Rating | | | | |
|---|---|---|---|---|---|
| Prototype ID | Compression Resistance (Wet) | Cohesiveness | Moldability | Flexibility | Strength |
| Formulation 1 | 4 | 4 | 3 | 3 | 4 |
| Formulation 2 | 4 | 4 | 3 | 3 | 4 |
| Formulation 3 | 2 | 5 | 5 | 2 | 1 |
| Formulation 4 | 2 | 3 | 2 | 2 | 2 |
| Formulation 5 | 5 | 4 | 3 | 4 | 5 |

1 = poor; 2 = below average; 3 = average; 4 = above average; 5 = excellent

TABLE 4

| Results of Physical Handling | |
|---|---|
| Prototype ID | Comments |
| Formulation 1 | Dry: There were some flakes in the vial Wet: Soaked up more than 95% of 5 cc blood. Minimum granule loss when manipulated. Compression resistant. After manipulating, bounces back to its original shape (good shape memory property). Bends well. |
| Formulation 2 | Dry: There were some flakes in the vial Wet: Soaked up more than 95% of 5 cc blood. Minimum granule loss when manipulated. Compression resistant. After manipulating, bounces back to its original shape (good shape memory property). Bends well. Similar handling characteristics as Formulation 1 |
| Formulation 3 | Dry: There were minimum flakes in the vial. Felt lighter, softer and fluffier compared to Formulations 1, 2, 4 and 5. No visible granules in the scaffold. Wet: Soaked 50% of 5 cc blood and shrunk. Turned in to putty. No particle loss during handling. Can be shaped in to a ball, rod, taco and other different shapes. Excellent putty. |
| Formulation 4 | Dry: There were some flakes in the vial Wet: Soaked up more than 90% of 5 cc blood. When manipulated falls apart and losses granules. Did not meet minimum expectations for handling characteristics. |
| Formulation 5 | Dry: There were some flakes in the vial Wet: Soaked up more than 95% of 5 cc blood. Minimum granule loss when manipulated. Compression resistant. After manipulating, bounces back to its original shape (good shape memory property). Bends well. Performed better than the other formulations. |

According to the results, Formulation 5 performed the best as a compression resistant matrix. This was followed by Formulation 1 and Formulation 2 (both showed similar handling properties). Formulation 3 acted as putty and is an excellent candidate for use in putty form. Formulation 4 did not exhibit desired handling properties.

EXAMPLE 2

Optimization of Collagen to Calcium Phosphate Ratio of Formulation 5

Preparation of the Materials

Six bone graft substitute formulation prototypes were manufactured with pepsin-treated collagen and variable collagen to calcium phosphate granule ratios and dehydrothermal treatment (DHT) time, according to Table 5. The particle size range of calcium phosphate granules was between 500 μm and 1000 μm. Lyophilization was followed by DHT treatment in all samples. Lyophilization was performed according to the lyophilization program in Example 1, Table 2. DHT temperature was 110° C. for all formulations. All prototypes were gamma sterilized (25-30 kGy). After sterilization, each prototype was hydrated in preparation of handling evaluation. Hydration of prototypes was performed by placing each prototype in a petri dish and soaking with 5 cc of heparinized sheep blood.

TABLE 5

| Prototype Formulations | | | | | | | |
|---|---|---|---|---|---|---|---|
| Prototype ID | Collagen Composition | Conc (mg/ml) | Collagen Final wt % | Granule Final wt % | Collagen Slurry (ml) | Granule (gr) | DHT |
| Formulation 5-1 | Pepsin Treated | 65 | 16 | 84 | 75 | 25 | 3 days |
| Formulation 5-2 | Pepsin Treated | 65 | 16 | 84 | 75 | 25 | 1 days |

TABLE 5-continued

Prototype Formulations

| Prototype ID | Collagen Composition | Conc (mg/ml) | Collagen Final wt % | Granule Final wt % | Collagen Slurry (ml) | Granule (gr) | DHT |
|---|---|---|---|---|---|---|---|
| Formulation 5-3 | Pepsin Treated | 65 | 16 | 84 | 75 | 25 | 2 hours |
| Formulation 5-4 | Pepsin Treated | 65 | 12 | 88 | 64 | 36 | 3 days |
| Formulation 5-5 | Pepsin Treated | 65 | 12 | 88 | 64 | 36 | 1 days |
| Formulation 5-6 | Pepsin Treated | 65 | 12 | 88 | 64 | 36 | 2 hours |

Physical Handling of the Samples

In order to determine the optimal ratio of collagen, granules, and DHT time for a sample, each prototype was evaluated based on its response to physical handling. Prototype samples were bended, twisted, pulled, and gently compressed to simulate handling conditions. Handling properties which were evaluated included compression resistance when wet, cohesiveness, moldability, flexibility, strength, and adhesiveness.

Handling properties of the prototypes were evaluated on a score from one (1) to five (5), with 1 being "poor" and 5 being "excellent." Each prototype was evaluated four (4) times, each time by a different individual.

Results of Physical Handling

Results of the physical handling of each prototype are shown in Tables 6 and 7.

TABLE 6

Handling Properties - Average Rating

| Prototype ID | Compression Resistance (Wet) | Cohesiveness | Moldability | Flexibility | Strength |
|---|---|---|---|---|---|
| Formulation 5-1 | 5 | 5 | 4 | 5 | 4 |
| Formulation 5-2 | 5 | 5 | 4 | 4 | 4 |
| Formulation 5-3 | 4 | 5 | 4 | 4 | 4 |
| Formulation 5-4 | 5 | 4 | 5 | 5 | 5 |
| Formulation 5-5 | 5 | 5 | 5 | 5 | 5 |
| Formulation 5-6 | 5 | 5 | 5 | 5 | 5 |

1 = poor; 2 = below average; 3 = average; 4 = above average; 5 = excellent

TABLE 7

Results of Physical Handling

| Prototype ID | Comments |
|---|---|
| Formulation 5-1 | Dry: Minimal amount of flakes present in the vial. Wet: Soaked up more than 90% of 5 cc blood (took about 8 to 10 minutes). Minimum granule loss when manipulated. Compression resistant. Moldable, flexible and strong when hydrated. |
| Formulation 5-2 | Dry: Minimal amount of flakes present in the vial. Wet: Soaked up more than 90% of 5 cc blood (took about 8 to 10 minutes). Minimum granule loss when manipulated. Compression resistant. Moldable, flexible and strong when hydrated. |
| Formulation 5-3 | Dry: Minimal amount of flakes present in the vial. Wet: Soaked up more than 90% of 5 cc blood (took about 8 to 10 minutes). Minimum granule loss when manipulated. Compression resistance was slightly lower than Formulations 5-1 and 5-2. Moldable, flexible and strong when hydrated. |
| Formulation 5-4 | Dry: Minimal amount of flakes present in the vial. Wet: Soaked up more than 90% of 5 cc blood (took about 6 to 8 minutes, faster than Formulations 5-1, 5-2 and 5-3). Minimum granule loss when manipulated. Compression resistant. After manipulating, bounces back to its original shape (good shape memory property). The best performer (same as Formulation 5-5) |
| Formulation 5-5 | Dry: Minimal amount of flakes present in the vial. Wet: Soaked up more than 90% of 5 cc blood (took about 6 to 8 minutes, faster than #1, 2, and 3 prototypes). Minimum granule loss when manipulated. Compression resistant. After manipulating, bounces back to its original shape (good shape memory property). The best performer (same as Formulation 5-4) |
| Formulation 5-6 | Dry: Minimal amount of flakes present in the vial. Wet: Soaked up more than 90% of 5 cc blood. Minimum granule loss when manipulated. Compression resistant. After manipulating, bounces back to its original shape (good shape memory property). Handling performance was slightly lower than Formulations 5-4 and 5-5 but still showed excellent handling characteristics. |

All prototypes performed well and demonstrated acceptable handling properties, but some prototypes performed better than others. Formulation 5-4 and Formulation 5-5 prototypes performed the best as a compression resistant matrix. While the following prototypes each had acceptable handling properties, their level of handling performance decreased in the following order: Formulation 5-6, Formulation 5-1, Formulation 5-2, Formulation 5-3. Results also indicated that prototypes having more granules resulted in a stiffer scaffold. Blood uptake of Formulation 5-4, 5-5 and 5-6 were faster than Formulation 5-1, 5-2 and 5-3. This may be attributed to higher granule content in Formulations 5-4, 5-5 and 5-6.

Discussion & Conclusions

According to the results, all prototypes showed acceptable handling characteristics, but Formulations 5-4 and 5-5 performed most optimally. Formulations 5-4, 5-5 and 5-6 were compression resistant. Whereas Formulations 5-4 and 5-5 had the most optimal handling characteristics, Formulation 5-6 also performed well and has significant manufacturing benefits as a result of its short DHT time.

EXAMPLE 3

Collagen Preparation

Four bone graft substitute prototypes were manufactured using 4 different calcium phosphate (CaP) granule lots, according to Table 8. Properties of each CaP granule lot are shown in Table 9. During manufacture, each sample was prepared using fresh collagen dough, and granules were mixed with collagen using a new blending technique.

The prototype samples were manufactured by using a new blending technique as follows. Low concentration collagen (LCC) and high concentration collagen (HCC) were prepared. Type I bovine collagen from tendon source treated with 0.05% pepsin was suspended in 10% isopropyl alcohol and mixed with 0.1N HCl. The soluble collagen was adjusted to the low (12.5 mg/g) and high (100 mg/g) concentration by controlling the amount of 10% isopropyl alcohol and HCl solution. The LCC was mixed with the calcium phosphate granules by hand and was left to sit for 30 minutes. The LCC/CaP granule slurry was then blended with the HCC by mixer for nine minutes. The final concentration of the collagen solution was 65 mg/g. At the end of the blending process, the collagen/granule mixture was poured into molds. Thus, each prototype has a composition as shown in Table 10.

The same lyophilization program was performed for each sample according to the lyophilization program in Example 1, Table 2. Lyophilization was followed by Dehydrothermal (DHT) treatment in all samples. DHT temperature was 110° C. for all samples. All prototypes were gamma sterilized (25-30 kGy). Each prototype underwent XRD analysis, SEM analysis and qualitative handling evaluation analysis to determine the effect of the new blending technique on granule phase composition and porosity.

TABLE 8

Bone Graft Substitute Prototypes

| Prototype ID | Calcium Phosphate Granule Lot # | Dimensions (L × W × H) |
| --- | --- | --- |
| Formulation A | 1 | 50 × 10.5 × 12 mm (±1 × ±1 × ±1 mm) |
| Formulation B | 2 | 50 × 10.5 × 12 mm (±1 × ±1 × ±1 mm) |
| Formulation C | 3 | 50 × 10.5 × 12 mm (±1 × ±1 × ±1 mm) |
| Formulation D | 4 | 50 × 10.5 × 12 mm (±1 × ±1 × ±1 mm) |

TABLE 9

Characteristics of CaP Granules

| CaP Granule Lot # | Granule Size | TCP % | Porosity % |
| --- | --- | --- | --- |
| 1 | 500-1000 μm | 94 | 75 |
| 2 | 500-1000 μm | 100 | 75.6 |
| 3 | 500-1000 μm | 100 | 68 |
| 4 | 500-1000 μm | 93 | 68 |

TABLE 10

Prototype Formulation

| Final Conc. (mg/g) of Collagen Solution | Collagen Final wt % | Granule Final wt % | DHT Duration |
| --- | --- | --- | --- |
| 65 | 12 | 88 | 24 hr |

3.1 X-Ray Diffraction (XRD) Analysis 3 samples of each prototype underwent XRD analysis and results are summarized in Table 6. All samples were within specification, TCP>90% and HA<10%. The combination of collagen with granules did not influence the granule composition.

TABLE 11

XRD Analysis Results

| Sample ID | | β TCP % | HA % | Other phases | Ca/P ratio |
| --- | --- | --- | --- | --- | --- |
| Formulation A | 1 | 94 | 6 | No | 1.51 |
| | 2 | 94 | 6 | No | 1.51 |
| | 3 | 94 | 6 | No | 1.51 |
| Formulation B | 1 | 96 | 4 | No | 1.51 |
| | 2 | 94 | 6 | No | 1.51 |
| | 3 | 95 | 5 | No | 1.51 |
| Formulation C | 1 | 100 | 0 | No | 1.50 |
| | 2 | 100 | 0 | No | 1.50 |
| | 3 | 100 | 0 | No | 1.50 |

3.2 Scanning Electron Micrograph (SEM) Analysis

Prior to SEM evaluation, 2 samples of each prototype were divided into smaller pieces and samples were fixed on a SEM sample stub and coated with gold-palladium to increase the conductivity of the samples. Per SEM evaluation, it is evident that surface morphology of granules did not change after mixing with collagen.

Qualitative Handling Evaluation

Each prototype sample was hydrated with 6 cc of heparinized sheep blood. Prior to handling evaluation, samples were kept in blood until most of the blood was absorbed by the sample. 3 samples of each prototype were evaluated by a total of 5 expert users. All of the evaluators agreed that the speed of blood uptake was very fast for all samples and, overall, all of the samples showed excellent handling properties. Handling characteristics are summarized in Table 12.

TABLE 12

Qualitative Handling Evaluation

| Prototype ID | Comments |
| --- | --- |
| Formulation A | Dry: Minimal amount of flakes present in the vial. Wet: Soaked up more than 95% of 6 cc blood within 90 seconds. Minimum granule loss when manipulated. Compression resistant. After manipulating, bounces back to its original shape. After longer manipulation, forms a cohesive and a workable putty. Minimal granule loss in putty form. |
| Formulation B | Dry: Minimal amount of flakes present in the vial. Wet: Soaked up more than 95% of 6 cc blood within 90 seconds. Minimum granule loss when manipulated. Compression resistant. After manipulating, bounces back to its original shape. After longer manipulation, forms a cohesive and a workable putty. Minimal granule loss in putty form. |
| Formulation C | Dry: Minimal amount of flakes present in the vial. Wet: Soaked up more than 95% of 6 cc blood within 90 seconds. Minimum granule loss when manipulated. Compression resistant. After manipulating, bounces |

TABLE 12-continued

Qualitative Handling Evaluation

| Prototype ID | Comments |
|---|---|
| | back to its original shape. After longer manipulation, forms a cohesive and a workable putty. Minimal granule loss in putty form. |

The blending technique described herein allows for the mixing of granules and collagen without any phase separation. Per XRD and SEM results, mixing the granules using the new technique results in no change in microstructure or phase composition of the granules. According to the qualitative handling evaluation, all samples soaked up most of the blood within 90 seconds. When the prototypes were manipulated, minimum granule loss was observed. All samples were compression resistant, and after compressing on each sample, all bounced back to their original shape. Additionally, when the samples were firmly compressed and manipulated by kneading and tearing, all samples showed a putty type of consistency. This formed putty was cohesive and when handled showed minimum granule loss, which is a desired property for a putty.

What is claimed is:

1. A method of making an osteoinductive bone graft substitute, comprising:
   mixing a first soluble collagen solution having a first concentration with osteoinductive calcium phosphate granules to create a slurry;
   blending the slurry with a second soluble collagen solution having a second concentration which is greater than the first concentration to create a mixture having a final collagen concentration of 65 mg/g;
   pouring the mixture into a mold; and
   lyophilizing the mixture.

2. The method of making an osteoinductive bone graft of claim 1, wherein the first collagen solution has a concentration of 12.5 mg/g.

3. The method of making an osteoinductive bone graft of claim 1, wherein the second collagen solution has a concentration of 100 mg/g.

4. The method of making an osteoinductive bone graft of claim 1, wherein the osteoinductive calcium phosphate comprises greater than 90% β-TCP and less than 10% hydroxyapatite.

5. The method of making an osteoinductive bone graft of claim 1, wherein the osteoinductive calcium phosphate comprises 100% β-TCP.

* * * * *